United States Patent [19]

Gäng et al.

[11] Patent Number: 4,966,152
[45] Date of Patent: Oct. 30, 1990

[54] TRANSDUCER

[75] Inventors: Achim Gäng, Stuttgart; Martin Schraag, Sindelfingen, both of Fed. Rep. of Germany; Günter Blendinger, Summerville, S.C.

[73] Assignee: Hewlett-Packard Company, Palo Alto, Calif.

[21] Appl. No.: 221,807

[22] Filed: Jul. 20, 1988

[30] Foreign Application Priority Data

Jul. 21, 1987 [EP] European Pat. Off. ........ 87110529.2

[51] Int. Cl.$^5$ ............................................... A61B 8/02
[52] U.S. Cl. ............................ 128/661.07; 128/775
[58] Field of Search .................. 128/661.07, 662.04, 128/698, 775

[56] References Cited

U.S. PATENT DOCUMENTS

| 3,379,901 | 4/1968 | Richards | 128/662.04 X |
| 3,587,561 | 6/1971 | Zicdonis | 128/662.04 |
| 3,824,988 | 7/1974 | Soldner et al. | 128/662.04 |
| 3,859,984 | 1/1975 | Langley | 128/662.04 |
| 4,640,295 | 2/1987 | Isaacson | 128/748 |
| 4,781,200 | 11/1988 | Baker | 128/775 X |

FOREIGN PATENT DOCUMENTS

| 0027215 | 10/1980 | European Pat. Off. | |
| 2343709 | 3/1975 | Fed. Rep. of Germany | |
| 2826391 | 1/1980 | Fed. Rep. of Germany | |
| 134815A | 11/1972 | United Kingdom | 128/662.04 |

Primary Examiner—Francis Jaworski

[57] ABSTRACT

A transducer for extra-uterine monitoring of fetal heart rate and labor activity comprises a casing the lower portion of which carries ultrasound crystals. Additional crystals are carried by a movable base plate which is connected with tension-measuring means.

7 Claims, 3 Drawing Sheets

TRANSDUCER

BACKGROUND OF THE INVENTION

The present invention relates to a transducer for extra-uterine monitoring of fetal heart rate during pregnancy and labor, with a transducer casing the lower portion of which carries a plurality of piezo-electric crystals arranged to emit and/or receive ultrasound waves with wide-beam characteristics.

In gynecology and obstetrics, two medical parameters are important to assess the condition of the fetus. These two parameters are the fetal beat-to-beat heart rate—e.g. measured via an ultrasound doppler signal—and uterus (or labor) activity. Simultaneous assessment of the fetal heart rate (FHR) and uterus activity (Toco) allows an exact determination of the fetal condition. Monitors measuring and recording both parameters are called cardiotocographs (CTG monitors).

Under second stage labor and birth, the fetal heart rate may be obtained directly by a fetal scalp electrode. Uterus activity may be measured by an intrauterine pressure transducer. Although both measuring principles lead to excellent signals, they require intravaginal measurement and are therefore not applicable for checks during pregnancy.

For pre-birth applications, the fetal heart rate may therefore be obtained by an ultrasound (US) transducer which is to be placed externally on the pregnant woman's abdomen (there are also further methods to obtain the fetal heart rate externally like measuring the heart sound, but the ultrasound method is the most common one). The ultrasound signal is received by piezo-electric crystals and appropriately filtered. As the heart rate signal is contained in the—very noisy—received ultrasound doppler signal, the ultrasound transducer must be placed directly over the fetal heart, i.e. on the lower left part of the abdomen.

Uterus activity is obtained by means of a tocodynamometer (toco transducer) which is to be placed externally on the fundus uteri, i.e. approximately centrally on the abdomen. That transducer is a tension measuring device, most commonly one or more resistive wire strain(s). The theory of what is really measured by these transducers is complex as uterus "hardness" as well as uterus deformation (and sometimes also respiration) influence the tension, but still it is possible to obtain clinically relevant results, i.e. to discover contraction frequency and shape.

For clinical checks during pregnancy and in the first stage of birth, both external (US and Toco) transducers have to be placed on the abdomen, but at different places as described above. Each of these transducers must be fixed with a rubber belt. This procedure is time and material consuming as well as unpleasant for the pregnant woman.

One has therefore just tried to combine transducers. A very early cardiotocograph had a transducer which measured the fetal heart rate via the heart sound by means of a moving coil as well as uterus activity by means of a movable bolt the position of which was sensed by a differential transformer. This combination transducer was very weighty (approximately 1.5 kilograms), difficult to apply and uncomfortable for the woman. Furthermore, the fetal heart rate signal was not stable as measuring the heart sound did not yield a reliable signal (in particular as the transducer could not be placed in its optimum position—it had to be placed in a medium position between the optimum points for heart rate and uterus activity). Some women additionally complained about hematoma caused by the movable bolt.

Therefore, one returned to separate transducers for fetal heart rate and uterus activity as described above.

It is a major objective of the present invention to provide a transducer which combines both fetal heart rate and uterus activity measuring means in one housing but still does not comprise the disadvantages of the earlier combination transducer.

According to one aspect of the invention, a transducer for extra-uterine monitoring of fetal heart rate during pregnancy and labor, with a transducer casing the lower portion of which carries a plurality of piezo-electric crystals arranged to emit and/or receive ultrasound waves with wide-beam characteristics comprises additionally tension measuring means supported by said transducer casing for the purpose of measuring labor activity, said tension-measuring means being connected with a movable base plate; furthermore, said base plate carries at least one piezo-electric crystal.

In former ultrasound transducers, the ultrasound beam had a relatively small diameter (approx. 3 centimeters) in order to obtain a meaningful heart rate signal not covered by other noise contained in the ultrasound signal. These ultrasound transducers had to be placed exactly over the fetal heart with the ultrasound beam hitting the heart.

Since several years, wide-beam ultrasound transducers are available. These transducers emit an ultrasound beam with diameter of 4 cm or more (typically 6 cm) and are therefore easier to apply. Still the fetal heart rate can be obtained reliably as the received ultrasound signal is filtered by an auto-correlation filter.

BRIEF SUMMARY OF THE INVENTION

The present invention is, among other, based on the finding that it is possible to use such a wide-beam ultrasound transducer even when not exactly focussed on the fetal heart. Therefore, the transducer may be placed on the abdomen with some displacement to the optimum position. If the transducer is placed between the optimum position for fetal heart rate recognition and the optimum position for toco recognition (the fundus uteri), both parameters may be measured with one transducer provided means for toco recognition can also be integrated into the transducer. This is provided by the present invention.

In a transducer according to the present invention, tension-measuring means are integrated in the transducer housing which are connected with a movable base plate. This base plate is situated in the lower portion of the transducer housing and serves as a "mechanical receiver". The forces exerted on the base plate are transmitted to the tension-measuring means.

Such combination of ultrasound and tension-measuring means in one casing is only possible if the tension-measuring means do not impair the quality of the ultrasound signal. To obtain a sufficient ultrasound beam, it is mandatory that at least one crystal is positioned centrally in the transducer. On the other hand, the movable base plate is arranged in the central position of the transducer.

It is an important finding of the present invention that, in contrast to what was expected, a piezoelectric crystal (as a transmitter and/or receiver of ultrasound waves) supported by the movable base plate does not have negative impact on the generated ultrasound field and on the received ultrasound signals. The ultrasound field is hardly deformed by the piezoelectric crystal(s) movably supported by the base plate even if there are further crystals fixed to the transducer housing and not to said base plate. On the other hand, even if the transducer comprises only crystals fixed on the base plate, movement of said base plate does not impair the received ultrasound signal and the fetal heart rate signal.

Therefore, the present invention provides a combination transducer which is not only light and easy to handle but also yields high quality signals. The new transducer is easy to manufacture and comfortable for the pregnant woman.

As outlined above, the piezo-electric crystals may be carried only by the base plate or, additionally, also by the remaining lower portion of the transducer casing. Of course, one may use transmitter and receiver crystals or crystals which provide both operating modes.

Preferably the base plate is carried out as part of the outer contour of said transducer casing to facilitate transducer application. A guide plate connected with the base plate by studs may guide base plate movement; that guide plate is connected with the tension measuring means. Advantageously the edges of the base plate are movably connected with the transducer casing and, in particular, this movable connection is provided by an elastomer film spanned over the lower portion of the transducer casing and the base plate. Such a film ensures easy movement and guidance of the base plate and protects the inner cavities of the transducer from soiling e.g. by ultrasonic contact gel.

In a preferred embodiment, the base plate and/or the adjoining part of the transducer casing is/are curved at its/their bottom side(s). Such a design increases the aperture angle of the ultrasound beam so that the fetal heart lies within this beam even if the transducer is placed on the pregnant woman's abdomen with some displacement to its optimum position.

The tension-measuring means may be, for example, a resistive wire strain bridge, a piezo-resistive semiconductor or the like.

Intensive evaluations revealed that a homogenous ultra sound field can be achieved by means of the new transducer if a piezo-electric crystal is positioned centrally on the base plate and—surrounded by a circle of six equally-spaced crystals on said base plate. On the outer ring of the transducer casing surrounding said base plate six other equally-spaced crystals are positioned, but with an angle rotation of 30° with reference to the ring of crystals on the base plate.

BRIEF DESCRIPTION OF THE DRAWING

A transducer embodying the present invention will now be described with reference to the accompanying drawings in which.

DETAILED DESCRIPTION OF THE INVENTION

Figure 1:
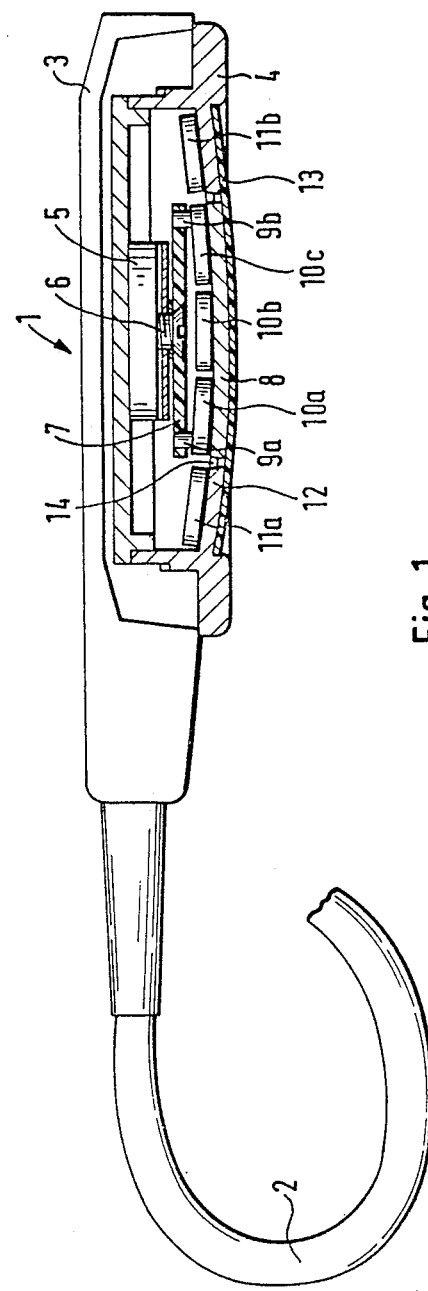
FIG. 1 is a cross-section of a transducer according to the present invention.

According to FIG. 1, there is shown an ultrasound-/toco-transducer. The transducer casing is generally outlined as, 1. The transducer casing is connected with a monitor via a cable 2.

The transducer casing consists of a cover 3 and a lower part 4. Cover 3 carries a resistive wire strain component 5; this component comprises four resistive wire strains connected as bridge circuit to measure mechanical motion. A screw 6 connects the resistive wire strain component with a guide plate 7 which is connected with a base plate 8 with studs 9a, 9b.

Base plate 8 carries piezo-electric crystals 10a to 10c. Other crystals 11a, 11b are carried by a ring 12 which is part of the lower portion 4 of the transducer casing. These crystals serve as ultrasound transmitting and receiving elements.

FIG. 1 shows that the bottom side of base plate 8 and the ring 12 of lower portion 4 carrying crystals have a curved surface. Said curved surface is covered by an elastomer film 13 which ensures mechanical stability and covers gap 14 between ring 12 and base plate 8. Therefore, ultrasonic contact gel applied to the bottoms side cannot creep into gap 14.

The bottom side of transducer casing 1 is applied to the pregnant woman's abdomen in a position between the optimum positions for fetal heart rate and toco as will be explained by means of FIG. 4, and the curved surface guarantees a good contact to the skin. Base plate 8 senses mechanical motion of the abdomen and transmits it to resistive wire strain component 5 via guide plate 7 to give an indication of uterus activity. Piezoelectric crystals 10a to 10c and 11a, 11b set up a widebeam ultrasonic field, and the reflected ultrasonic waves are used to determine the fetal heart rate by means of an autocorrelation filter. The ultrasonic field generated by the piezo-electric crystals is rather homogenous even if base plate 8 is moving.

Figure 2:
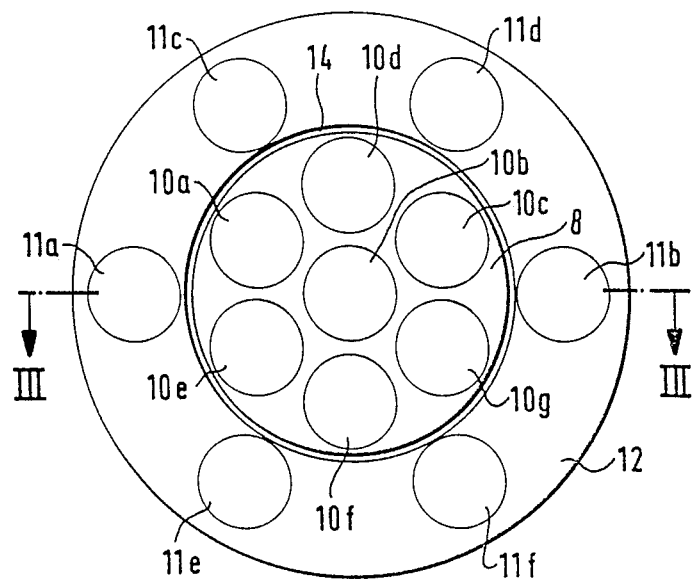
FIG. 2 is a bottom view of the lower portion of said transducer.

FIG. 1 shows only some of the crystals in cross-section. The complete arrangement of crystals is depicted in FIG. 2 which is a bottom view of ring 12 and base plate 8. Base plate 8 carries a central crystal 10b and six equally-spaced crystals 10a and 10c to 10g. Outer ring 12 also carries a ring of equally-spaced crystals 11a to 11f which are rotated around 30° with reference to the inner ring. Base plate 8 and ring 12 are separated by gap 14.

Figure 3:
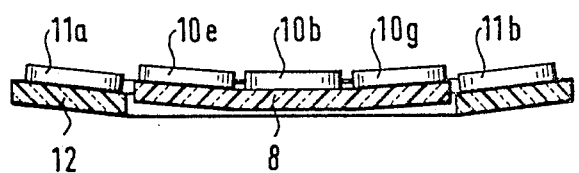
FIG. 3 is a cross-section along line III—III of FIG. 2.

A cross-section along line III—III of FIG. 2 is shown in FIG. 3. This figure shows base plate 8 in a shifted position.

Figure 4:
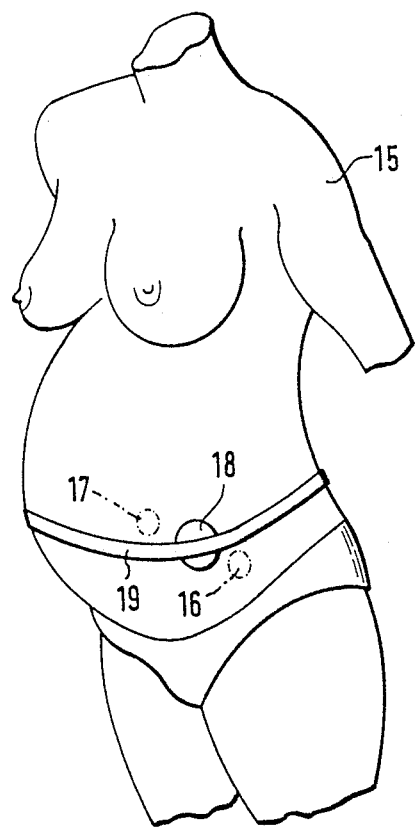
FIG. 4 is a schematic diagram of a pregnant woman's body indicating transducer positions.

FIG. 4 depicts positioning of the new transducer on a pregnant woman's 15 abdomen. The optimum position for a separate ultrasound transducer is indicated by 16 and the optimum position for the toco transducer is referred to 17. The new transducer may now be positioned in a medium position indicated by 18 without any negative impact on the received signals. The transducer is fixed by a rubber belt 19.

We claim:

1. A transducer for extra-uterine monitoring of fetal heart rate and uterus activity during pregnancy and labor comprising:

a casing having a cover an sides extending from one side of said cover, strain detection means mounted on said one side of said cover for providing signals in response to movement of an input member therof, a base plate, means between said cover and said base plate for mechanically coupling said base plate to said input member so that movement of said base plate moves said input member, a piezo-electric crystal centrally mounted on said base plate, a plurality of piezo-electric crystals mounted on said base plate around said piezo-electric crystal, means forming a ring extending inwardly from said sides, and forming a space between it and said base plate, and another plurality of piezo-electric crystals mounted around said ring.

2. A transducer as set forth in claim wherein the crystals of said second plurality of piezo-electric crystals are mounted at angular positions midway between the angular positions of the crystals of said first mentioned plurality of crystals.

3. A transducer as set forth in claim 1 wherein the external surfaces of said base plate and ring that are on the sides thereof opposite said cover are coextensive.

4. A transducer as set forth in claim 3 wherein said external surfaces are convex with respect to said cover.

5. A transducer as set forth in claim 3 further comprising:

an elastomer film adhered to said external surfaces of said base plate and ring so as to cover the space between said base plate and said ring.

6. A transducer for extra-uterine monitoring of fetal heart rate and uterus activity during pregnancy and labor comprising:

A casing having a cover and sides extending from one side of said cover, strain detection means mounted on said one side of said cover for providing signals in response to movement of an input member thereof, a base plate, means between said cover and said base plate for mechanically coupling said base plate to said input member so that movement of said base plate moves said input member, a piezo-electric crystal centrally mounted on said base plate, means forming a ring extending inwardly from said sides, and forming space between it and said base plate, and a plurality of piezo-electric crystals mounted around said ring.

7. A transducer for extra-uterine monitoring of fetal heart rate and uterus activity that can be located at a point on a mother's abdomen that is between the optimum position for each type of monitoring comprising:

A casing comprised of a cover and sides extending from one side of said cover strain detection means mounted on said one side of said cover for producing a signal in response to forces applied to it, a base plate extending in a direction transverse to said sides, means for mechanically coupling said base plate to said strain detection means in such manner as to couple forces to said detection means when said base plate changes its distance from or its angular position with respect to said cover, at least one peizo-electric crystal mounted on said base plate so as to have an acoustic axis extending generally perpendicularly to said base plate, means forming a ring extending inwardly from said sides that is contiguous with said base plate, and a plurality of crystals mounted on said ring, said plurality of crystals having acoustic axis extending generally perpendicularly to said ring, whereby tilting of said base plate with respect to said ring has little effect on the shape of the acoustic field produced by all of said crystals.

* * * * *